US012558135B2

(12) United States Patent
Lacaze

(10) Patent No.: US 12,558,135 B2
(45) Date of Patent: Feb. 24, 2026

(54) OSSEOUS ANCHORING IMPLANT WITH CORTICAL STABILIZATION

(71) Applicant: LOCK IN SA, Rolle (CH)

(72) Inventor: Guillaume Lacaze, La Rippe (CH)

(73) Assignee: LOCK IN SA, Rolle (CH)

( * ) Notice: Subject to any disclaimer, the term of this patent is extended or adjusted under 35 U.S.C. 154(b) by 0 days.

(21) Appl. No.: 17/871,268

(22) Filed: Jul. 22, 2022

(65) Prior Publication Data

US 2022/0354558 A1     Nov. 10, 2022

Related U.S. Application Data

(62) Division of application No. 17/093,985, filed on Nov. 10, 2020, now Pat. No. 11,426,224.

(30) Foreign Application Priority Data

Apr. 9, 2020    (FR) ...................................... 2003579

(51) Int. Cl.
*A61B 17/86*        (2006.01)
*A61B 17/84*        (2006.01)
*A61B 90/00*        (2016.01)

(52) U.S. Cl.
CPC ........ *A61B 17/8685* (2013.01); *A61B 17/844* (2013.01); *A61B 17/8625* (2013.01); *A61B 90/39* (2016.02)

(58) Field of Classification Search
CPC .......................... A61B 17/8685; A61B 17/844
See application file for complete search history.

(56) References Cited

U.S. PATENT DOCUMENTS

| | | | | |
|---|---|---|---|---|
| 6,668,688 B2 * | 12/2003 | Zhao | .................. | A61B 17/8685 |
| | | | | 81/439 |
| 2008/0039846 A1 * | 2/2008 | Lee | ...................... | A61B 17/686 |
| | | | | 433/7 |

FOREIGN PATENT DOCUMENTS

| | | |
|---|---|---|
| EP | 2603163 A1 | 6/2013 |
| WO | 2012045787 A1 | 4/2012 |

* cited by examiner

*Primary Examiner* — Olivia C Chang
(74) *Attorney, Agent, or Firm* — Studebaker Brackett PLLC

(57) ABSTRACT

An osseous anchoring implant with cortical stabilization, including an expandable sleeve having a first threading inside and a second threading outside, a screw having an external profile complementary to the internal profile of said expandable sleeve and an external threading with a reverse screw pitch of the second threading. The implant switching from a folded rest position to a deployed position by the actuation of said reversed threadings, causing the penetration of the screw into the expandable sleeve and generating the radial expansion of said expandable sleeve by deformation on a distal portion. In the deployed position, the expandable sleeve has a frustoconical shape. The proximal portion of the screw includes an outer osseous anchoring threading and a frustoconical portion whose flaring is reversed relative to that of the expandable sleeve in the deployed position.

12 Claims, 8 Drawing Sheets

[Fig. 1a]
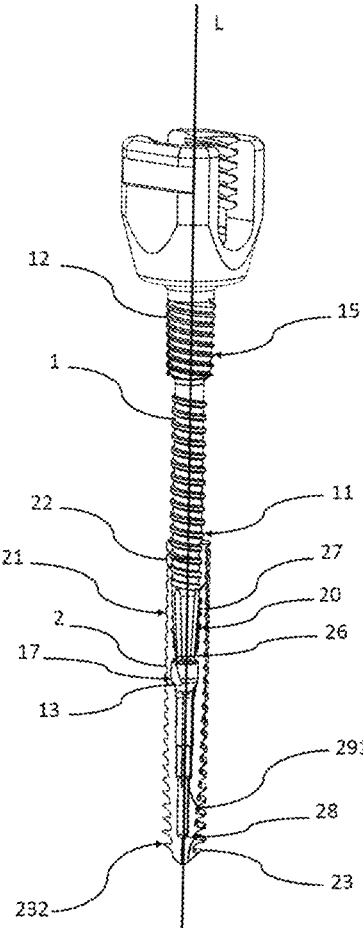
[Fig. 1b]
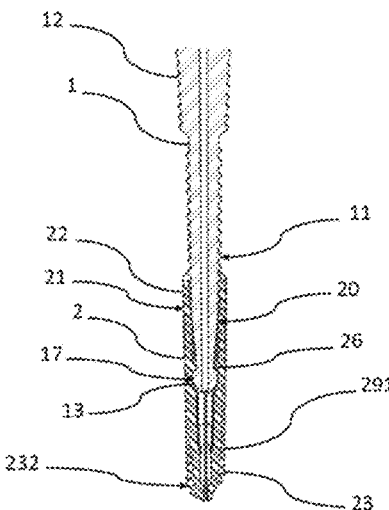

[Fig. 2]
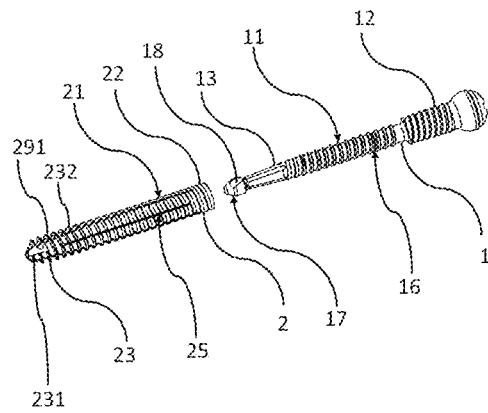
[Fig. 3a]
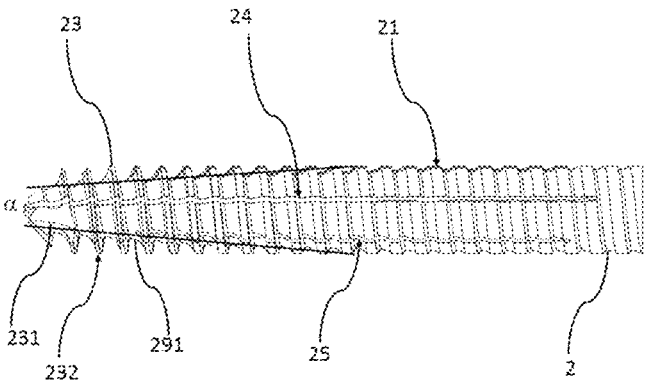
[Fig. 3b]
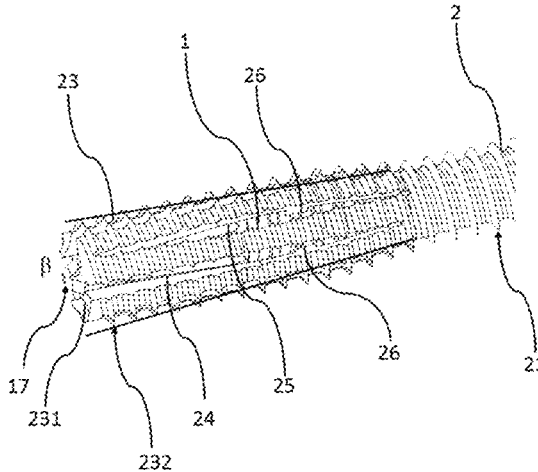

[Fig. 3c]
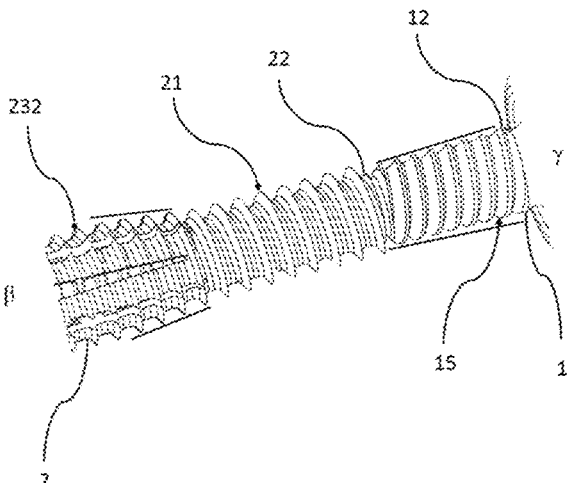
[Fig. 4a]
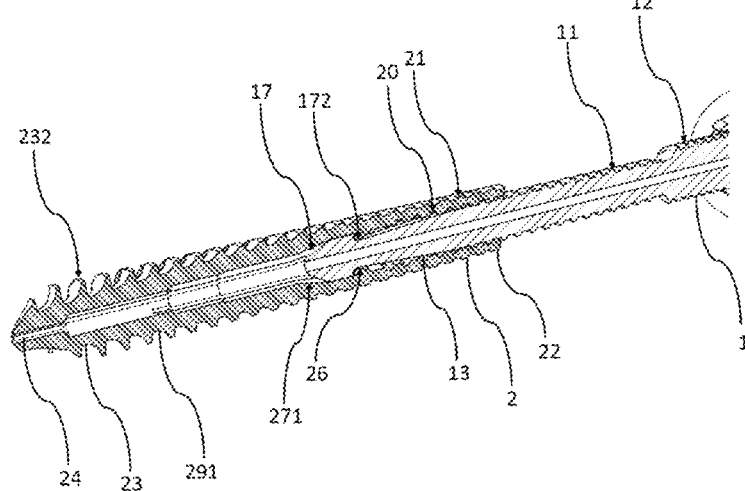

[Fig. 6]
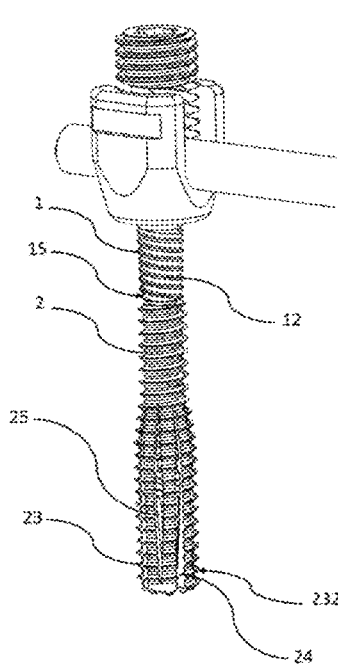
[Fig. 7]
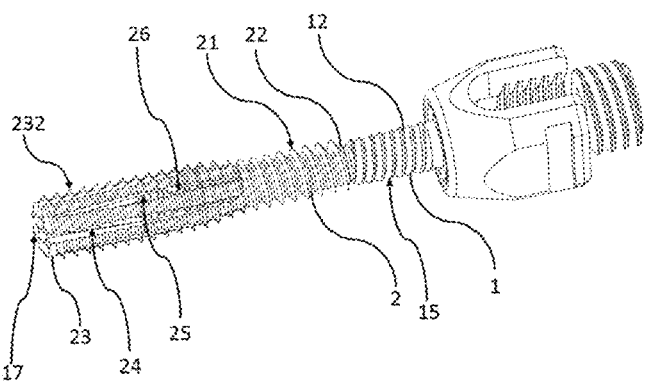
[Fig. 8]
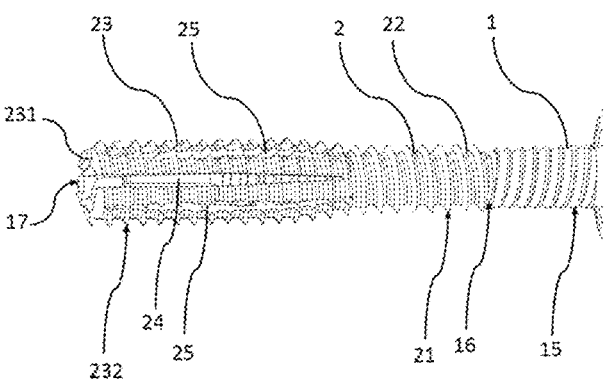

[Fig. 9]
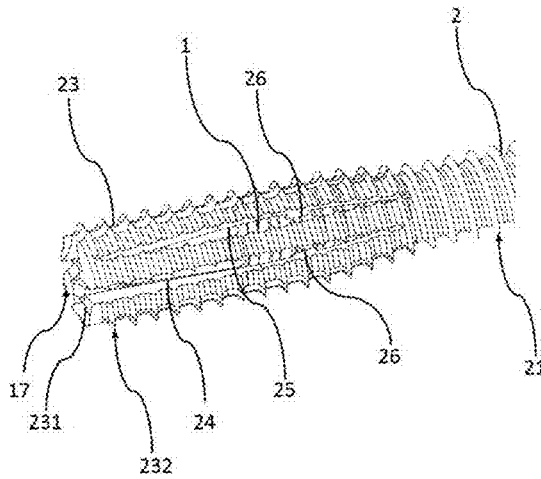
[Fig. 10a]
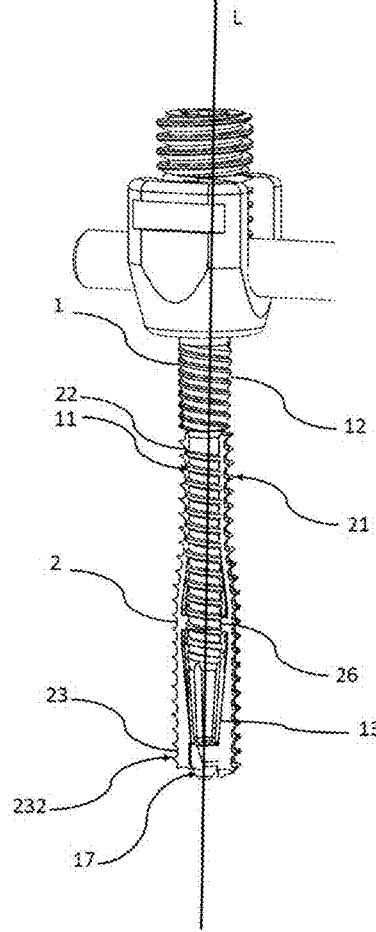

[Fig. 10b]
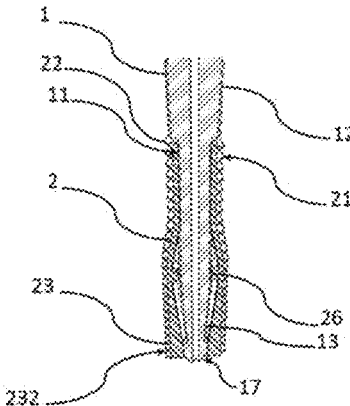
[Fig. 11]
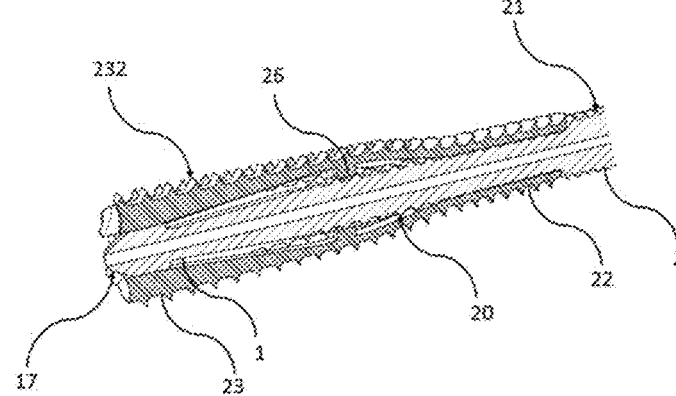

[Fig. 12]
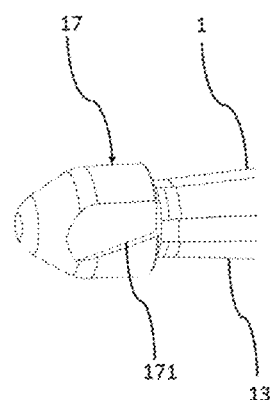
[Fig. 13]
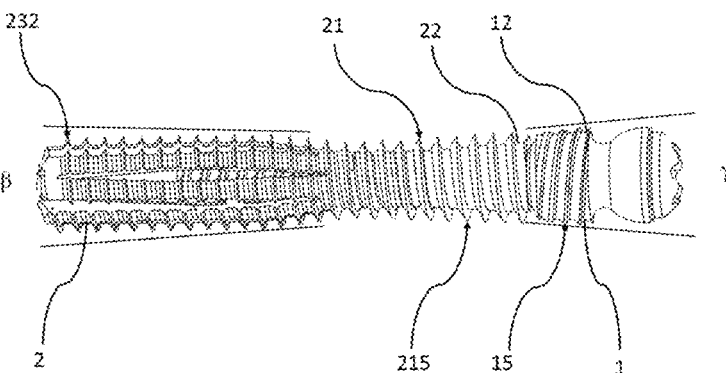

OSSEOUS ANCHORING IMPLANT WITH CORTICAL STABILIZATION

The present application is a divisional of U.S. application Ser. No. 17/093,985, filed Nov. 10, 2020, which claims priority to French Application No. 2003579, filed Apr. 9, 2020, the entirety of each of which are incorporated herein by reference.

TECHNICAL FIELD AND OBJECT OF THE INVENTION

The present invention relates to the field of osseous implants for dental, orthopedic, surgical or osteoplastic applications, such as orthopedic screws alone or with plates, dental or ligament implants for joints such as for example the hips, the elbows, the ankles, the shoulders and the knees, or rachidian spinal implants for example for the vertebrae. These fields of application are given by way of example and are not restrictive as to the scope of the present invention.

More specifically, the invention relates to an osseous implant whose implantation in the porous bone is extremely stable.

STATE OF THE ART

An osseous anchoring implant generally consists of an elongate body intended to be implanted in a housing formed in an osseous tissue, such as the jaw bone for a dental application or in a vertebra for example.

It is important that the osseous anchoring implant can be easily introduced into the osseous tissue, without creating damage, and that the anchoring device inside the osseous tissue is stable. Indeed, current osseous anchoring implant devices do not allow anchoring without generating more cracks or damage than required for the size of the device itself in the osseous tissue, moreover it is necessary that the fixation in the osseous implant is reliable and extremely stable, because many therapeutic techniques today rely on bone growth that generally requires that the devices anchored in the osseous tissue remain as immobile as possible.

In addition, it is also necessary that the implantation in the osseous tissue is easy to perform in order to avoid any risk of incorrect positioning of the osseous implant, which could in particular be due to a difficulty in the positioning or in the implantation in the bone.

In addition, in the event of a fall, impact or accident, it is important that the implant remains in place in the osseous tissue, that is to say it does not move through the bone. For this, a very high stability of the implant is necessary.

The state of the art comprises the patent document EP2603163 B1, which describes an endosseous implant with improved anchoring able to be implanted in an osseous tissue and including a fixing device comprising a part called gripping part in the osseous tissue, and a part called expansion part, these two parts being movable relative to each other. The invention mentioned in this patent also comprises cooperating mechanical connection means disposed, on the one hand, on the gripping part and, on the other hand, on the expansion part, such that the relative mobility of the two parts comprises at least one degree of freedom and such that a relative displacement of said two parts causes a widening of the gripping part, said widening causing the gripping of the gripping part in the osseous tissue. The osseous implant described in this patent particularly finds application in the dental field. However, such a solution has drawbacks because the osseous implant, although immobilized in rotation and in translation in the tissue, presents the risk of moving, in particular of receding during an impact.

The invention therefore aims at solving these drawbacks by proposing an osseous implant able to be implanted and immobilized in the osseous tissue in an extremely stable manner.

GENERAL PRESENTATION OF THE INVENTION

The present invention therefore aims at overcoming the drawbacks of the prior art by proposing an osseous anchoring implant, hereinafter called osseous implant, which is easily implantable in the osseous tissue and stable.

To achieve this result, the present invention relates to an osseous anchoring implant with cortical stabilization able to be implanted in an osseous tissue, comprising:

an expandable sleeve extending between a proximal portion having a first internal diameter, and a distal portion having a second internal diameter smaller than said first internal diameter, these two portions defining a longitudinal axis and said first and second internal diameters defining an internal profile of said expandable sleeve, and comprising at least a first threading inside the expandable sleeve and at least a second threading outside the expandable sleeve, a screw body extending between a proximal portion and a distal portion and having along said longitudinal axis (L), an external profile complementary to the internal profile of said expandable sleeve and at least one external threading whose screw pitch is reversed relative to said second external threading of the expandable sleeve, the implant being able to switch from a folded rest position to a deployed position by the actuation of said reversed threading by causing the penetration of the screw into the expandable sleeve and generating the expansion of said expandable sleeve by deformation, thanks to the fact that said second internal diameter of the expandable sleeve comprises, at the distal portion, at least a shrinkage having a size inferior to the external diameter of the screw, in the deployed position of the implant, the second internal diameter of the expandable sleeve being greater than or equal to the first proximal diameter of the sleeve, the sleeve having a cylindrical shape or a frustoconical portion obtained by said expansion, the implant having, in the vicinity of its proximal portion in the deployed position, a proximal frustoconical portion flaring towards the proximal portion and formed:

Either by the external profile of said sleeve,

Or by the external profile of said screw body,

Or by the shape complementary of the external profiles of the sleeve and of the screw body, in the deployed position, said proximal frustoconical portion having an outer osseous anchoring threading over its periphery.

According to a feature, said at least one shrinkage is located at a distance from the proximal portion along the longitudinal axis determined as a function of the depth, in the osseous tissue, at which the expansion of the expandable sleeve is desired.

According to one feature, the screw is implanted in the osseous tissue by sinking inside the expandable sleeve, its proximal portion comprising the outer osseous anchoring threading is implanted in the osseous tissue and having a frustoconical outer profile on its proximal portion whose cone opening angle is reversed relative to that of the frustoconical portion of the expandable sleeve in the deployed position.

According to another feature, the screw is implanted in the osseous tissue by sinking inside the expandable sleeve, its proximal portion comprising the outer osseous anchoring threading is implanted in the osseous tissue and has an outer cylindrical profile on its proximal portion.

According to another feature, said frustoconical portion of the proximal portion of the expandable sleeve and said frustoconical outer profile of the screw are positioned facing each other.

According to another feature, the angle of the frustoconical portion of the proximal portion of the expandable sleeve is greater than the angle of the frustoconical outer profile of the screw to allow greater flaring and improve the primary stability.

According to another feature, the screw comprises at least one distance marker to visualize the moment when the screwing of the screw in the expandable sleeve must be carried out in the opposite direction to the screwing of the expandable sleeve into the osseous tissue.

According to another feature, the distance marker is a laser marker.

According to another feature, the thread height of the second external threading of the expandable sleeve is greater than that of the mechanical threading of the first threading inside the expandable sleeve and of the external threading of the screw.

According to another feature, the distal portion of the expandable sleeve has a frustoconical portion comprising a threading with a conical core allowing the expandable sleeve to sink deep into the bone.

According to another feature, the distal portion includes self-tapping notches.

According to another feature, the expandable sleeve includes longitudinal through-slots extending up to its distal portion.

According to another feature, there are as many self-tapping notches as there are longitudinal through-slots.

According to another feature, the expandable sleeve includes longitudinal non-through slots.

According to another feature, the screw comprises at its distal portion a tip including at least one rear flute with cutting edge whose angle relative to a longitudinal axis (L) defined by the two ends extending between the proximal portion and the distal portion of the expandable sleeve, is determined as a function of the direction of rotation of the screw during the unscrewing from the deployed position to the rest position, to mill the bone during the extraction of the osseous implant.

The invention also relates to a method for placing an osseous implant as briefly described above, the method comprising the following steps:

Screwing the osseous implant in the direction of the external threading of the expandable sleeve until the distance marker is flush with the surface of the bone cortex, Screwing the osseous implant by screwing in the direction of the second threading of the screw to complete the screwing of the threaded screw into the bone and to proceed with the expansion of said expandable sleeve.

According to one feature, the cortical bone is perforated by means of a cortical preform tool.

According to another feature, the invention also relates to a method for extracting an osseous implant as briefly described above, the method comprising the following steps:

Unscrewing the osseous implant in the direction of the external threading until the appearance of a distance marker, Locking the implant by a clamp blocking the screw in the expandable sleeve in the rest position, Unscrewing the implant in the direction of the second threading.

According to one feature, the extraction method comprises an additional screwing before unscrewing the osseous implant.

PRESENTATION OF THE FIGURES

Other characteristics and advantages of the invention will appear upon reading the detailed description of the embodiments of the invention, given by way of example only, and with reference to the drawings which show:

FIG. 1 *a*, FIG. 1*b* and FIG. 2 represent a detailed view of the elements that make up the osseous implant according to the invention.

FIG. 3*a* represents a detailed view of the expandable sleeve before the expansion according to the invention.

FIG. 3*b* represents a detailed view of the expandable sleeve after expansion according to the invention.

FIG. 3*c* represents a detailed view of the proximal frustoconical portion in the deployed position formed by the external profile of the sleeve, according to the invention.

FIG. 4*a* and FIG. 4*b* represent a diagram of a cross-section of the interior of the osseous implant sleeve, before the expansion of the expandable sleeve according to the invention.

FIG. 5 represents a detailed view of the proximal frustoconical portion in the deployed position formed by the external profile of the screw, according to the invention.

FIG. 6 and FIG. 7 represent a diagram of the osseous implant in the expanded position, according to the invention.

FIG. 8 and FIG. 9 represent a view of the expandable sleeve in the expanded position according to the invention.

FIG. 10*a*, FIG. 10*b* and FIG. 11 represent a view of the interior of the osseous implant in the expanded position according to the invention.

FIG. 12 represents a diagram of the tip of the screw according to the invention.

FIG. 13 represents a detailed view of the proximal frustoconical portion in the deployed position formed by the external profiles of the screw and of the sleeve, according to the invention.

DETAILED DESCRIPTION OF ONE EMBODIMENT OF THE INVENTION

Various embodiments of the invention are described below in particular with reference to the illustrative and non-limiting figures.

The present application relates to the implantation of an osseous implant in an osseous tissue.

It should be noted here that the term "implantation" designates the fact of introducing the osseous implant into the osseous tissue, generally by screwing. The implantation proposed in the present application designates a sufficiently solid and stable introduction of the osseous implant to ensure good maintenance of this osseous implant in the osseous tissue.

In addition, the term "osseous tissue(s)" generally designates all types of bones, whether they are compact bones (such as the cortical bone or the periosteum) or cancellous (soft, porous) bones, because the osseous implant system of the present application is implantable in any type of osseous tissue. In addition, the terms used should not be interpreted in their general meaning but rather in the light of the functional considerations detailed in the present application.

FIG. 1a, FIG. 1b and FIG. 2 are illustrative and non-limiting exemplary embodiments of the osseous implant.

As for example represented in FIG. 1a, FIG. 1b and FIG. 2, an osseous implant able to be implanted in an osseous tissue comprises: an expandable sleeve (2) extending between a proximal portion (22) and a distal portion (23), the ends of these two portions defining a longitudinal axis (L), and comprising, on the one hand, at least a first threading (20) inside the expandable sleeve (2) and, on the other hand, at least a second threading (21) outside the expandable sleeve (2).

The terms "proximal" and "distal" designate in the present application, respectively, the part where the implantation device is held to allow its implantation in the osseous tissue, and the part which is implanted first in the osseous tissue (opposite the proximal portion).

The terms "proximal and distal portions" designate in the present application the parts located in the vicinity of the distal and proximal ends.

In the present application, the term "expandable sleeve (2)" generally designates a hollow generalized cylinder.

In some embodiments, the osseous implant also comprises a screw (1) extending between a proximal portion (12) and a distal portion (13) on an axis collinear with the axis (L) and having, on the one hand, along said longitudinal axis (L), an external profile complementary to the internal profile of said expandable sleeve (2) and, on the other hand, at least one external threading (11) whose screw pitch is reversed relative to said second external threading (21) of the expandable sleeve (2).

It should be noted that the proximal portion (12) of the screw (1) is directly implanted in the cortical bone.

In some embodiments, the proximal end of the screw (1) comprises an actuating means making it possible to screw the screw (1), said actuating means comprising a structure of any shape desirable by the practitioner depending on the use which will be made of it, as for example represented in FIG. 1b. The actuating means being for example a hexagonal hole or a torx or a cruciform or any other actuating means, and the proximal end of the screw (1) may have various shapes depending on the desirable destination for the osseous anchoring implant (head for fixing a polyaxial or non-polyaxial osteosynthesis bar, or for fixing a plate or any other device).

In some embodiments, the screw (1) comprises a cannula passing through the screw (1) to allow the practitioner to inject for example cement, if he considers this necessary.

It should also be noted that the osseous implant is made of titanium or of implantable medical stainless steel or of polyetheretherketone (PEEK) or of polyetherketoneketone (PEKK) or any other material of which those skilled in the art can determine the suitability depending on its mechanical, physico-chemical properties and on its biocompatibility.

In some embodiments, the screw (1) comprises a cannula passing through the screw (1) to allow the practitioner to inject for example cement, if he considers it necessary In some embodiments, the second threading (21) outside the expandable sleeve (2) allows osseous anchoring. The term "osseous anchoring" used in the present application generally designates various types of devices comprising at least one element intended to enter the osseous tissue along a rectilinear path, under the action of a push generally exerted in the form of repeated screwing operations, impacts or strikes. It is known that an osseous anchoring threading has a thread height generally greater than that of a mechanical threading to ensure better anchoring. In addition, an osseous anchoring threading is generally different from a mechanical threading and those skilled in the art know that, depending on the type of bone and desired application, it is possible to vary the diameter of the core, the screw pitch and the wire height and the present application covers these various embodiments. The thread height of the second external threading (21) of the expandable sleeve (2) is greater than that of the mechanical threading of the first threading (20) inside the expandable sleeve (2) and the external threading (11) of the screw. (1). Thus, the second threading (21) comprises higher edges than the first threading (20) to allow the osseous implant to enter and be anchored in the bone.

In addition, in some embodiments, some mechanical threads, such as trapezoidal threads, offer less resistance which facilitates the penetration of the screw (1) into the expandable sleeve (2) anchored in the bone. The trapezoidal thread also allows distributing the large load of the osseous tissue in compression against the osseous implant.

Figures 4B, 5:
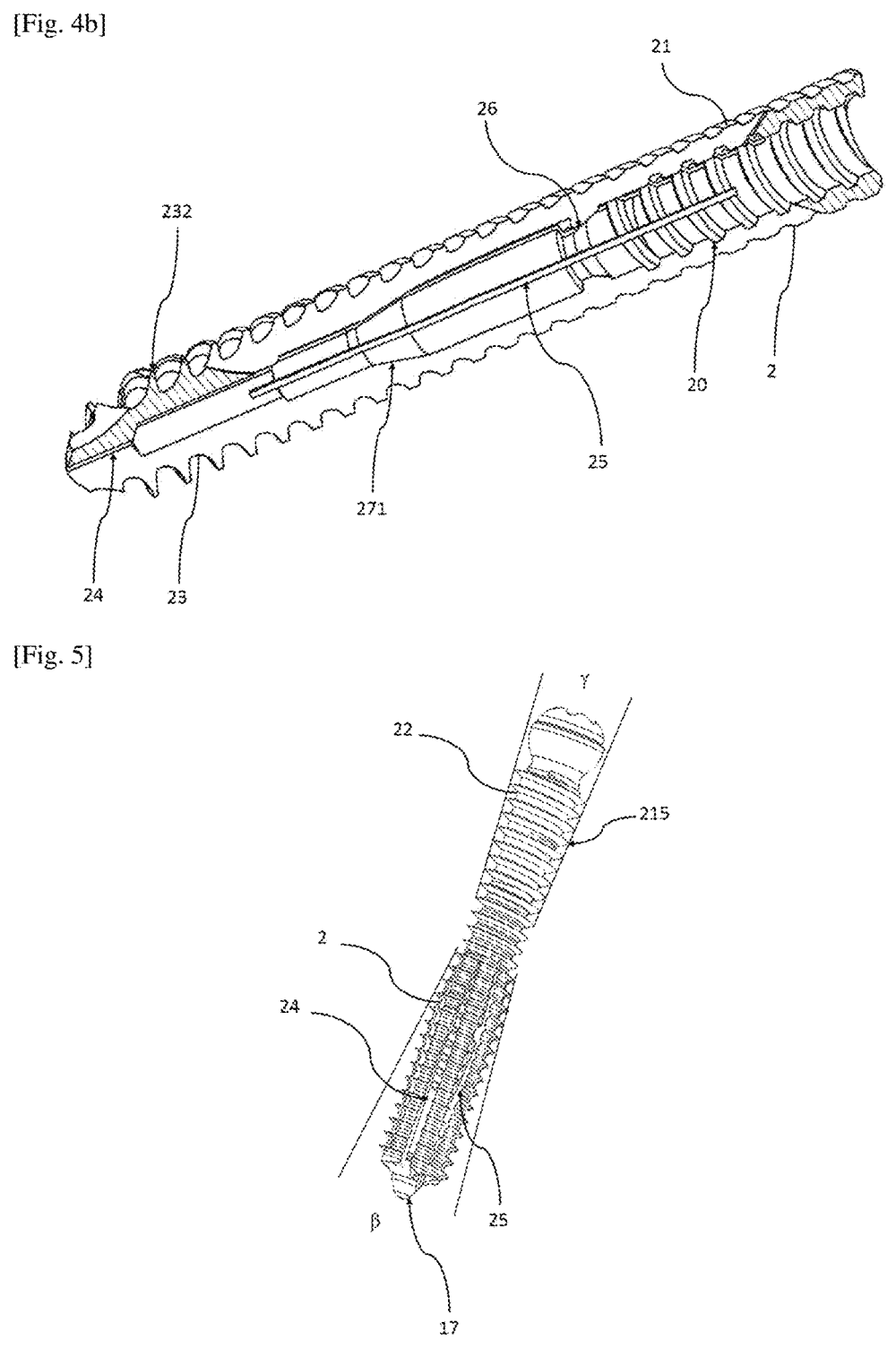

In some embodiments, the distal portion (23) of the expandable sleeve (2) has a frustoconical portion (291) comprising a threading (232) with a conical core allowing the expandable sleeve (2) to sink deep into the bone, as for example represented in FIG. 1a to FIG. 4b.

In some embodiments, the distal portion (23) of the sleeve (2) is self-tapping and includes self-tapping (milling and tapping) notches (231), as for example represented in FIG. 3a to FIG. 4b. This distal portion (23) allows preserving the bone during the implantation while avoiding pre-drilling before insertion of the implant, and thus allows keeping a maximum amount of bone around the implanted area, which improves the stability of the osseous implant. Indeed, the osteointegration time is thus reduced, which limits the need to add any type of bone filling material, whether synthetic or natural. In addition, the distribution of the notches (231) ensures a good balance over each of the parts of the distal portion (23) and thus a good uniformity of the distribution of the force during the insertion of the implant into the osseous tissue.

In some embodiments, the screw (1) comprises at least one distance marker (16), as for example represented in FIG. 2, to visualize the moment when the screwing of the screw (1) in the expandable sleeve (2) must be carried out in the opposite direction to the screwing of the expandable sleeve (2) into the osseous tissue.

In some embodiments, the distance marker (16) is a laser marker.

In some embodiments, placing the implant comprises the following steps:

Screwing the osseous implant in the direction of the external threading (21) until the distance marker (16) is flush with the surface of the bone cortex, Screwing the osseous implant by screwing in the direction of the second threading (11) to complete the screwing of the threaded screw (1) into the bone and proceed with the expansion of said expandable sleeve (2).

In some variants of the invention, the cortical bone is perforated by means of a cortical perform tool.

The present application also relates to the expansion of an osseous implant in the osseous tissue.

In some embodiments, the external profile of the screw (1) and the internal profile of the expandable sleeve (2) are complementary, so that they provide, in an expanded configuration:

A proximal bearing point supported by the complementarity of the outer diameter of the screw (1) with the inner diameter of the expandable sleeve (2), A distal bearing point supported by the cooperation between the expandable sleeve (2) whose inner diameter narrows towards the distal portion until becoming smaller than the outer diameter of the screw (1), and the screw (1), A "central" bearing point located between these two bearing points, formed by the cooperation between the outer diameter of the screw (1) and the inner diameter of the expandable sleeve (2) which induce an outer diameter of the expandable sleeve (2) at the "central" level which is greater than the outer diameter of the expandable sleeve (2) at the proximal bearing point.

In some embodiments, as for example represented in FIG. 4a and FIG. 4b, the implant is able to switch from a folded rest position to a deployed position by the actuation of the reversed threadings by causing the penetration of the screw (1) into the expandable sleeve (2) and by generating the expansion of said expandable sleeve (2) by deformation, thanks to the fact that the external diameter of the screw (1) is greater than the internal diameter of the expandable sleeve (2), by at least one shrinkage (271) on a distal portion.

In some embodiments, the shrinkage (271) is located, relative to the proximal portion and along the longitudinal axis (L), at a distance determined as a function of the depth, in the osseous tissue, at which said expansion is desired. It should be noted that said distance is determined by the practitioner himself in particular with regard to the bone cortex and/or to the desired compression, as for example represented in FIG. 4a and FIG. 4b.

In some embodiments, the intermediate portion between the proximal end and the distal end of the expandable sleeve (2) whose duct is greater than the diameter of the place where the central bearing point is located, has a diameter difference.

In some embodiments, the duct of the expandable sleeve (2) of the intermediate portion between the proximal end and the distal end has a non-continuous slope. Thus, the shrinkage (271) can be located at a variable distance from the proximal end to offer an expansion at various depths, depending on the type of bone for example.

In some embodiments, the proximal portion of the screw (1) includes: an outer osseous anchoring threading (15), as for example represented in FIG. 1a, FIG. 1b and FIG. 2.

In some embodiments, the screw (1) is implanted in the osseous tissue by sinking inside the expandable sleeve (2), its proximal portion comprising the outer osseous anchoring threading (15) is implanted in the osseous tissue and has a frustoconical portion whose flaring is reversed relative to the flaring of the proximal portion of the expandable sleeve (2) in the deployed position, such as for example represented in FIG. 11. The reversal of the flaring of the two truncated cones requires compression and/or friction that improve(s) the stability of the implant, in particular by the fact that these two truncated cones are located around the bone cortex.

In some embodiments, the screw (1) is implanted in the osseous tissue by sinking inside the expandable sleeve (2), its proximal portion comprising the outer osseous anchoring threading (15) is implanted in the osseous tissue and has a cylindrical portion or any offset shape.

The opposite inverted double cone obtained allows a gradual implantation of the implant by distributing the forces of the osseous implant in the osseous tissue during the implantation, allowing the transmission of the forces on a conical surface and not on a cylindrical line. In addition, the opposite inverted double cone ensures axial locking on the cortical part of the densest vertebra. It thus contributes to the hyper-stability of the osseous implant in the osseous tissue.

In some embodiments, as for example represented in FIG. 3a, the expandable sleeve (2) has an acute angle $\alpha$ at the end of its distal portion (23). This angle $\alpha$ opens and increases as the screw (1) enters the expandable sleeve (2), during the expansion.

In some embodiments, as for example represented in FIG. 3b, the angle $\alpha$, opening increasingly during the expansion, becomes an angle $\beta$, the angle $\beta$ being the angle of the expanded expandable sleeve (2).

In some embodiments, as for example represented in FIG. 3c, the cortical part compresses the osseous implant and the cortical part has an angle $\gamma$ carried by the expandable sleeve (2) or by the screw (1) or by both. The angle $\alpha$, by opening increasingly, becomes the angle $\beta$ of the expandable sleeve (2) and opposes the angle $\gamma$.

It will be noted that in the deployed position, the walls of the expandable sleeve (2) can in some embodiments be parallel instead of creating an angle $\beta$.

In some embodiments, the expandable sleeve (2) has a domed shape at the central bearing point, as for example represented in FIG. 5, by the presence of the angles $\alpha$ and $\beta$.

Indeed, in some embodiments, the implant is expandable between, on the one hand, a rest configuration in which an abutment mechanism (26) interlocks said expandable sleeve (2) and said screw body (1) thanks to the reversal of these two screw pitches, as for example represented in FIG. 1a, FIG. 1b, FIG. 4a, FIG. 4b, FIG. 6, FIG. 8 to FIG. 10b and, on the other hand, an expanded configuration obtained by the actuation of said complementary internal and external threadings of the expandable sleeve (2) and of the screw (1) mutually, causing the penetration of the screw (1) in the expandable sleeve (2) and generating the expansion of said expandable sleeve (2), thanks to the external diameter of the screw (1) which is greater than the internal diameter of the expandable sleeve (2), at least on a distal portion, by deformation of the expandable sleeve (2) during the penetration of the screw (1) into the expandable sleeve (2).

In some embodiments, in the deployed position of the implant, the second distal diameter of the expandable sleeve (2) is greater than or equal to the first proximal diameter of the sleeve (2), so that the sleeve (2) has a cylindrical shape or a frustoconical portion obtained by said expansion.

The implant has, in the vicinity of its proximal portion in the deployed position, a proximal frustoconical portion flaring towards the proximal portion and formed:

Either by the external profile of said expandable sleeve (2), as for example represented in FIG. 3c in the modes where the angle $\gamma$ is carried by the expandable sleeve (2), Or by the external profile of said screw body (1), as for example represented in FIG. 5 in the modes where the angle $\gamma$ is carried by the screw (1), Or by the shape complementary of the external profiles of the sleeve (2) and of the screw body (1), in the deployed position, as for example represented in FIG. 13 in the modes where the angle $\gamma$ is carried by the screw (1) and the expandable sleeve (2).

Said proximal frustoconical portion having an outer osseous anchoring threading (15, 215) over its periphery.

In some embodiments, in the deployed position of the implant, the expandable sleeve (2) has a frustoconical shape on at least one proximal portion (22), as for example represented in FIG. 5 to FIG. 10*b*, flaring towards the distal portion of the screw (1), in the vicinity of its proximal portion.

In some embodiments, the expandable sleeve (2) has a cylindrical or conical shape on at least one proximal portion (22).

In some embodiments, the screw (1) comprises a tip (17) on the tip of the distal portion (13), as for example represented in FIG. 1*a*, FIG. 1*b*, FIG. 2, FIG. 5, FIG. 10*a*, FIG. 10*b* and FIG. 12, whose external profile is complementary to the internal profile of the distal portion (23) of the expandable sleeve (2).

In some embodiments, said frustoconical portion of the proximal portion of the expandable sleeve (2) and said frustoconical outer profile of the screw (1) are positioned end to end or facing each other and connected to the proximal portion (22) of the expandable sleeve (2), the angle of said frustoconical portion of the proximal portion of the expandable sleeve (2) being greater than the angle of said frustoconical outer profile of the screw (1) to allow greater flaring and/or facilitate the expansion of the whole.

In some embodiments, as for example represented in FIG. 2, FIG. 3, FIG. 5, FIG. 6, FIG. 7 and FIG. 8, the expandable sleeve (2) includes longitudinal through-slots (24) extending up to its distal portion (23) and longitudinal non-through slots (25) allowing the expansion of the expandable sleeve (2). It is preferable that there are several through (24) or non-through (25) slots, and that the distal portion (23) includes the two types of slots, that is to say longitudinal through slots (24) and longitudinal non-through slots (25).

In some embodiments, the synergy between the through-slots (24) and the non-through slots (25) also allows truncated cone geometry and/or a domed shape in the deployed position.

In some embodiments, there are as many self-tapping notches (231) as there are longitudinal through-slots (24).

In some embodiments, the through-slots (24) and the non-through slots (25) are positioned offset relative to each other over the length of the expandable sleeve (2). The offset of the through-slots 24 and non-through slots 25 over the length improves the flexibility and the mechanical strength of the expandable sleeve (2) during the expansion.

In some variants of the invention, an extension of the osseous anchoring (15, 215) is possible.

In some embodiments, the longitudinal through (24) and non-through (25) slots on the distal portion (23) allow the cylindrical expansion of the expandable sleeve (2). The longitudinal non-through slots (25) contribute to the stability of the osseous implant in the osseous tissue by allowing, during the expansion, to be able to maintain the contact profile on the three bearing points between the expandable sleeve (2) and the screw (1), and by allowing the forces due to the expansion to be uniformly distributed over the periphery of the expanded expandable sleeve (2). The longitudinal through (24) and non-through (25) slots allow a radial expansion of the proximal portion (22) of the expandable sleeve (2) by complying with the elastic limit of the material of the expandable sleeve (2) and its elastic shrinking during unscrewing.

In some embodiments, said longitudinal through-slots (24) extend over 10 to 90% of the length of the expandable sleeve (2).

In some embodiments, as for example represented in FIG. 3*a*, the portion of the expandable sleeve (2) includes a taper angle alpha (α) at the bottom of the thread ensuring self-centering of the expandable sleeve (2) in the cavity made by the anatomical conical preform tool with the shape of the expandable sleeve (2) during the screwing operation.

According to one alternative embodiment (not represented), the screw (1) does not comprise a cortical threaded part. This variant allows making a shorter screw (1) and expandable sleeve (2) assembly adapted to other implantation circumstances.

Those skilled in the art understand that various types of tips and structures can be added onto the proximal portion of the screw (1), according to other assembly modes by adapting the shape of this portion for this purpose and according to the object of the implant. By way of non-limiting examples, these assemblies can be made by screws, clipping, keying, bonding or welding.

The osseous implant proposed in the invention can therefore be implanted quickly and accurately in the osseous tissue, and remain implanted in a very stable manner in the osseous tissue.

The present application describes various technical characteristics and advantages with reference to the figures and/or to various embodiments. Those skilled in the art will understand that the technical characteristics of a given embodiment can indeed be combined with characteristics of one or more other embodiment(s) unless the reverse is explicitly mentioned or these characteristics are incompatible or the combination does not work.

More generally, combinations of various types of implant retaining means and/or spine retaining means are envisaged and will be appreciated by those skilled in the art using the functional and structural considerations provided in the present application. In addition, the technical characteristics described in a given embodiment can be isolated from the other characteristics of this mode unless the reverse is explicitly mentioned, in particular because the functional considerations provided in the present application will provide a sufficient explanation so that the structural adaptations possibly necessary are within the reach of those skilled in the art.

Those skilled in the art, upon reading the present application, will understand that embodiments in many specific forms other than those described in detail are possible without departing from the field of application of the invention as claimed. Therefore, the present embodiments should be considered by way of illustration, but can be modified in the field defined by the scope of the appended claims, and the invention should not be limited to the details given above.

The invention claimed is:

1. An osseous implant with cortical stabilization able to be implanted in a bone, comprising:

an expandable sleeve extending between a proximal portion having a first internal diameter, and a distal portion having a second internal diameter smaller than said first internal diameter, these two portions defining a longitudinal axis and said first and second internal diameters defining an internal profile of said expandable sleeve, and comprising at least a first threading inside the expandable sleeve and at least a second threading outside the expandable sleeve, a screw body extending between a distal portion and a proximal portion having a head for fixing a plate on said bone, and having, along said longitudinal axis, an external profile complementary to the internal profile of said expandable sleeve and at least one external threading whose screw pitch is reversed relative to said second external threading of the expandable sleeve, wherein the implant is able to switch from a folded rest position to a deployed position by the actuation of said reversed threading by causing the penetration of the screw into the expandable sleeve and generating the expansion of said expandable sleeve by deformation, thanks to the fact that said second internal diameter of the expandable sleeve comprises at least one shrinkage having a size inferior to the external diameter of the screw, said shrinkage being located at a distance from the proximal end which is determined as a function of the desired expansion location relative to the cortical bone tissue, in the deployed position of the implant, the second internal diameter of the expandable sleeve being greater than or equal to the first internal diameter of the sleeve, and the external diameter of the expandable sleeve thereby being expanded, at the level of said shrinkage, to a diameter greater than the external diameter of the sleeve at the proximal portion.

2. The implant according to claim 1, wherein said at least one shrinkage is located at a distance from to the proximal portion and along the longitudinal axis (L) determined as a function of the depth, in the osseous tissue, at which the expansion of the expandable sleeve is desired and depends on the bone tissue in which the implant is intended to be anchored, in particular with regard to the bone cortex and/or to the desired compression exerted by the implant into the bone, between the expanded portion and the plate fixed by the implant.

3. The implant according to claim 1, wherein the screw is implanted in the osseous tissue by sinking inside the expandable sleeve, its proximal portion comprising the outer osseous anchoring threading is implanted in the osseous tissue and has an outer cylindrical profile on its proximal portion.

4. The implant according to claim 1, wherein the screw comprises at least one distance marker to visualize the moment when the screwing of the screw in the expandable sleeve must be carried out in the opposite direction to the screwing the expandable sleeve into the osseous tissue.

5. The implant according to claim 4, wherein the distance marker is a laser marker.

6. The implant according to claim 1, wherein the thread height of the second external threading of the expandable sleeve is greater than that of the mechanical threading of the first threading inside the expandable sleeve and of the external threading of the screw.

7. The implant according to claim 1, wherein the distal portion of the expandable sleeve has a frustoconical portion comprising a threading with a conical core allowing the expandable sleeve to sink deep into the bone.

8. The implant according to claim 1, wherein the distal portion includes self-tapping notches.

9. The implant according to claim 8, wherein the expandable sleeve includes longitudinal through-slots extending up to the distal portion.

10. The implant according to claim 9, wherein there are as many self-tapping notches as there are longitudinal through-slots.

11. The implant according to claim 1, wherein the expandable sleeve includes longitudinal non-through slots.

12. The implant according to claim 7, wherein the screw comprises at its distal portion a tip including at least one rear flute with cutting edge whose angle relative to a longitudinal axis defined by the two ends extending between the proximal portion and the distal portion of the expandable sleeve, is determined as a function of the direction of rotation of the screw during the unscrewing from the deployed position to the rest position, to mill the bone during the extraction of the osseous implant.

\* \* \* \* \*